(12) United States Patent
Edmunds

(10) Patent No.: US 9,357,982 B2
(45) Date of Patent: Jun. 7, 2016

(54) TAMPON ASSEMBLY

(76) Inventor: Kathleen Edmunds, Knoxville, TN (US)

( * ) Notice: Subject to any disclaimer, the term of this patent is extended or adjusted under 35 U.S.C. 154(b) by 247 days.

(21) Appl. No.: 13/507,883

(22) Filed: Aug. 3, 2012

(65) Prior Publication Data

US 2014/0039342 A1 Feb. 6, 2014

(51) Int. Cl.
*A61F 13/20* (2006.01)
*A61F 13/34* (2006.01)
*A61B 10/02* (2006.01)
*A61F 2/00* (2006.01)
*A61B 10/00* (2006.01)

(52) U.S. Cl.
CPC ............... *A61B 10/02* (2013.01); *A61F 2/005* (2013.01); *A61F 13/2045* (2013.01); *A61F 13/34* (2013.01); *A61B 2010/0074* (2013.01)

(58) Field of Classification Search
CPC ............ A61B 2010/0074; A61F 13/2045; A61F 13/208
USPC ............................................ 604/18; 600/562
See application file for complete search history.

(56) References Cited

U.S. PATENT DOCUMENTS

| 2,087,610 | A | | 7/1937 | Scott | |
|---|---|---|---|---|---|
| 2,241,451 | A | | 5/1941 | Fist | |
| 2,823,669 | A | * | 2/1958 | Kunnas, Jr. | 128/837 |
| 3,128,767 | A | * | 4/1964 | Nolan | 604/330 |
| 3,216,422 | A | | 11/1965 | Steiger et al. | |
| 3,983,874 | A | * | 10/1976 | Davis et al. | 604/330 |
| 3,986,511 | A | * | 10/1976 | Olofsson et al. | 604/366 |
| 4,311,543 | A | * | 1/1982 | Strickman et al. | 156/224 |
| 4,497,317 | A | * | 2/1985 | Boschetti | 128/837 |
| 4,640,272 | A | | 2/1987 | Monett | |
| 4,821,741 | A | | 4/1989 | Mohajer | |
| 5,231,992 | A | * | 8/1993 | Leon | 600/572 |
| 5,295,984 | A | * | 3/1994 | Contente et al. | 604/317 |
| 5,718,675 | A | | 2/1998 | Leijd | |
| 5,928,184 | A | * | 7/1999 | Etheredge et al. | 604/15 |
| 6,126,616 | A | | 10/2000 | Sanyal | |
| 6,168,609 | B1 | * | 1/2001 | Kamen et al. | 606/193 |
| 6,796,973 | B1 | | 9/2004 | Contente et al. | |
| 7,824,383 | B2 | * | 11/2010 | Sokal et al. | 604/285 |
| 2005/0171455 | A1 | * | 8/2005 | Turner | 600/569 |
| 2005/0256484 | A1 | | 11/2005 | Chase et al. | |

FOREIGN PATENT DOCUMENTS

WO WO 02/40912 A2 5/2002

* cited by examiner

*Primary Examiner* — Susan Su
(74) *Attorney, Agent, or Firm* — Michael E. McKee

(57) ABSTRACT

A tampon assembly includes a flexible and relatively thin impermeable portion having two opposite side faces and an outer edge which is oval in shape so that the oval shape of the impermeable portion has a largest dimension as measured through the center of the impermeable portion and a smallest dimension as measured through the center of the impermeable portion, and the largest dimension is at least about 1.5 times the size of the smallest dimension. The assembly further includes an absorbent pad portion which is secured to one side face of the impermeable portion so that when the assembly is positioned within a user, the absorbent pad portion is positioned in a condition for absorbing fluids and the outer edge of the impermeable portion sealingly engages the walls of the vaginal canal.

16 Claims, 3 Drawing Sheets

TAMPON ASSEMBLY

BACKGROUND OF THE INVENTION

This invention relates generally to feminine hygiene products and relates, more particularly, to tampon devices.

Inasmuch as tampon devices are commonly used by women to prevent the unwanted discharge of vaginal fluids through the vaginal canal, not all tampons of the prior art are equally-suited for this purpose. Firstly and in instances in which tampons comprised principally of a plug of absorbent material are used, the eventual saturation of the absorbent material prevents additional absorption of fluids. Therefore and in such instances, fluids are likely to migrate past such a tampon after the absorbent material becomes saturated. Secondly, there exists a diaphragm-class of tampon having a circular-shaped impervious membrane which is positionable within the vaginal canal for the intended purpose of preventing the passage of fluids which would otherwise flow through the canal. However, any poor fit-up between the edges of the membrane and the vaginal canal will not prevent the flow of fluids between the edge of the membrane and the walls of the canal and will, instead, likely promote user discomfort.

It would be desirable to provide a new and improved tampon assembly for preventing the unwanted discharge of vaginal fluids.

Accordingly, it is an object of the present invention to provide a new and improved tampon assembly which inhibits the flow of fluids through the vaginal canal.

Another object of the present invention is to provide such an assembly whose components provide an improved seal with the walls of the vaginal canal and effectively block the flow of fluids through the vaginal canal.

Still another object of the present assembly is to provide such an assembly whose componentry is adapted to collect and absorb fluids when the assembly is used and readily accepts the opening-defining end of the cervix.

Yet another object of the present invention is to provide such an assembly whose construction facilitates the positioning of the assembly into place.

A further object of the present invention is to provide such an assembly having a component which, if desired, can be recycled.

A still further object of the present invention is to provide such an assembly which promotes user comfort, can be used for birth control purposes, and does not inhibit vaginal intercourse.

A yet further object of the present invention is to provide such an assembly which can be used as a substitute for a pessary to help support the vaginal walls against deformation or displacement due to prolapse of, for example, the bladder, cervix or rectum.

One more object of the present invention is to provide such an assembly which can be used for collecting cervical cells for laboratory (e.g. pap smear) testing purposes.

Still one more object of the present invention is to provide such an assembly which is uncomplicated in structure, yet effective in operation.

SUMMARY OF THE INVENTION

This invention resides in a tampon assembly including a flexible and relatively thin impermeable portion having two opposite side faces and having an outer edge which is oval in shape so that the oval shape of the impermeable portion has a largest dimension as measured across the center of the impermeable portion and a smallest dimension as measured through the center of the impermeable portion, and the largest dimension is at least about 1.5 times the size of the smallest dimension. In addition, the assembly includes an absorbent portion which is secured to one side face of the impermeable portion so that when the assembly is positioned within a user for use, the absorbent portion is positioned to absorb fluids exiting the cervix, and the outer edge of the impermeable portion is disposed in sealing relationship with the vaginal walls of the user.

DETAILED DESCRIPTION OF AN ILLUSTRATIVE EMBODIMENT

Figure 1:
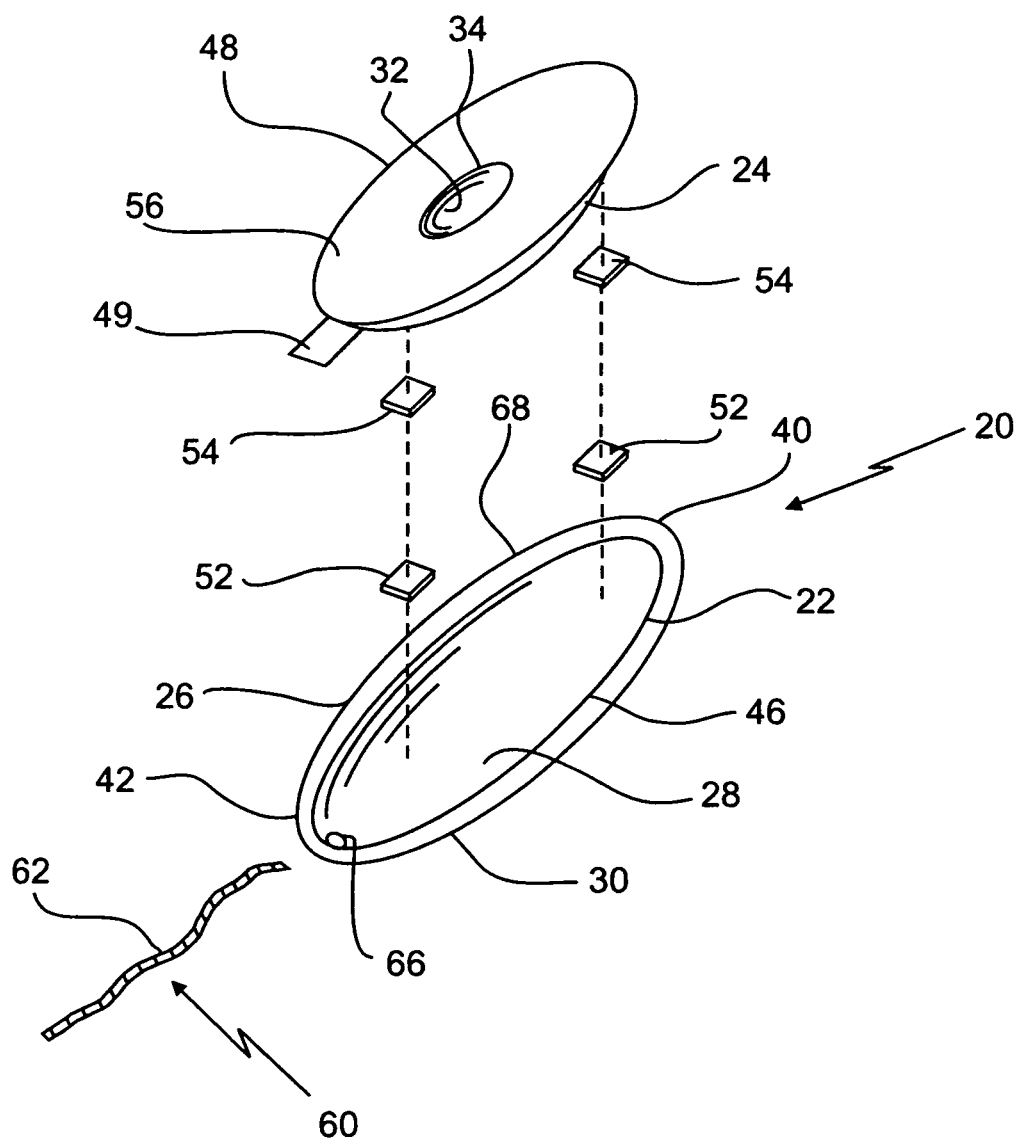
FIG. 1 is a perspective view of an embodiment of a tampon assembly within which features of the present invention are embodied and shown exploded.

Turning now to the drawings in greater detail and considering first FIG. 1, there is illustrated an embodiment, generally indicated 20, of a tampon assembly within which features of the present invention are embodied. The assembly 20 includes a liquid-impermeable portion 22 and an absorbent pad portion 24 which is releasably secured to the impermeable portion 22. As will be apparent herein, the absorbent portion 24 is adapted to absorb fluids which may exit the cervix of the user while the impermeable portion 22 of the tampon assembly 20 is adapted to provide a satisfactory seal between the outer edges of the impermeable portion 22 and the walls of the vaginal canal to prevent passage of fluids past the impermeable portion 22.

Although the assembly 20 is primarily described herein as being used for preventing the discharge of fluids from the vaginal canal, the assembly 20 can also be used in applications in which it is desired to strengthen the vaginal walls (from the inside thereof) to prevent deformation or displacement thereof. For example, there exists physical conditions, such as bladder prolapse, cervical prolapse or rectum prolapse, characterized by the displacement of various organs from their normal positions and which, in some instances, bear upon the vaginal walls. To counter the deleterious effects of such physical conditions, the assembly 20 can be positioned in its desired position along the vaginal canal to strengthen the walls of the vaginal canal and thereby resist displacement of the organs. Accordingly, the assembly 20 can be used as a substitute for a pessary which might otherwise be used as an aid in this regard.

Furthermore and because cervical cells are likely to accumulate, over a period of time, upon the surface of the absorbent portion 22 during use of the assembly 20, the assembly 20 can provide a means by which cervical cells of a patient are obtained for laboratory (e.g. pap smear) testing purposes. Accordingly, the principles of the present invention can be variously applied.

With reference to FIGS. 1-4, the impermeable portion 22 is saucer-shaped in form having a relatively shallow, concave side face 28 and an opposite convex side face 30. In addition, the impermeable portion 22 is relatively thin as measured between the side faces 28, 30. Moreover, the impermeable portion 22 possesses a degree of flexibility which permits the impermeable portion 22 (with the absorbent portion 24 secured thereto) to be folded about itself about its major, or longitudinal, axis (described herein) to facilitate the insertion of the assembly 20 into place (in a manner similar to the insertion of a diaphragm into place) and a degree of resiliency so that upon placement of the assembly 20 within the vaginal canal and upon subsequent release of the assembly 20 from its folded condition, the outer edges of the impermeable portion 22 resiliently flex outwardly from the major axis of the impermeable portion 22 and are biased, due to the resilient nature of the impermeable portion 22, against the walls of the user's vaginal canal.

To provide the impermeable portion 22 with a desired degree of flexibility and resiliency, the impermeable portion 22 can be constructed of any of a number of elastomeric materials, such as a relatively soft plastic, or other classes of materials, such as a coated paper. However, latex might be avoided as a choice of material for the impermeable portion 22 due to the allergic reaction that some individuals have to that material.

It is a feature of the assembly 20 that its impermeable portion 22 has an oval-shaped outer edge 26 (defining an inwardly-directed lip 27) to provide a better-fitting relationship between the outer edge 26 and the walls of the vaginal canal than can be had with circular-shaped portions of diaphragm-class of tampons of the prior art. In this connection, applicant, who is an obgyn physician, has discovered that in most females whom she has examined, the anterior-posterior dimension of the pelvis is greater than the transverse diameter of the pelvis. In other words and in order for the impermeable portion 22 to suitably fit within the vaginal canal and provide a desirable and comfortable sealing relationship with the walls of the canal, applicant has discovered that the front-to-back dimension of the impermeable portion 22 should be larger than the side-to-side dimension of the impermeable portion 22.

More specifically, the outer edge 26 of the impermeable portion 22 of the depicted assembly 20 (as best viewed in FIG. 3) is shaped to resemble an oval so that its maximum dimension (as measured along its major axis 36, indicated in phantom and extending through the center of the oval shape of the outer edge 26) is at least about 1.5 times the size of the minimum dimension (as measured along its minor axis 38, also indicated in phantom and extending through the center of the oval shape of the outer edge 26). Preferably, the oval-shaped outer edge 26 has a maximum dimension which is at least about 2.0 times the size of its minimum dimension. It has been found that the depicted assembly 20, with its oval-shaped impermeable portion 22, provides a better edge-to-vaginal canal sealing relationship than is capable of being formed with any impermeable portion of circular form and is advantageous in this respect.

While an oval, by definition, is symmetrical about at least one of its major or minor axes, the oval shape of the depicted impermeable portion 22 is symmetrical about each of its major and minor axes 36, 38. Therefore and more particularly, the shape of the outer edge 26 of the depicted impermeable portion 22 is elliptical. In a broad sense, therefore, the outer edge 26 of the impermeable portion 22 is oval, but in a preferred embodiment of the assembly 20, the outer edge 26 of the impermeable portion 22 is elliptical in shape.

The assembly 20, and more specifically, the impermeable portion 22, is intended to be inserted endwise into place through the vaginal canal as the impermeable portion 22 is folded about its major axis 36 and subsequently moved lengthwise (i.e. in a direction parallel to the major axis 36) through the canal. Accordingly and for present purposes, the leading end of the impermeable portion 22 (i.e. the end of the impermeable portion 22 which is inserted first through the vaginal canal 22) is indicted 40 in FIGS. 1-4, the opposite, or trailing, end of the impermeable portion 22 (i.e. the end of the impermeable portion 22 which follows the leading end 40 into place) is indicated 42 in FIGS. 1-4, and the opposite sides of the impermeable portion 22 which extend between the leading and trailing ends 40 and 42 are indicated 44 and 46 in FIGS. 1 and 4.

With reference again to FIGS. 1-3, the absorbent portion 24 is comprised of a substantially platen arrangement of soft absorbent material, such as a layup of cotton, rayon or a cotton/rayon blend of fibers, and is positionable against the concave side face 28 of the impermeable portion 22 for securement thereto. As best shown in FIG. 1, the absorbent portion 24 has an outer edge 48 which is shaped similar (i.e. oval-shaped) to that of the outer edge 26 and is centrally-disposed against the side face 28 of the impermeable portion 22 so that the outer edge 48 is captured beneath the inwardly-directed lip 27 of the impermeable portion 22. Accordingly, the outer edge 48 of the absorbent portion 24 is slightly smaller in size than the outer edge 26 so that when positioned against the side face 28, no part of the absorbent portion 24 extends outboard of the outer edge 26. With the absorbent portion 24 positioned against the side face 28, the total thickness of the assembly 20, as measured at its thickest point, is preferably no more than about 2.0 cm.

In addition, there is provided in the upwardly-facing surface, indicated 56, of the absorbent portion 22 a pre-formed concave indentation 32 which is centrally disposed therein. Within the depicted assembly 20, the concave indentation 32 has an outer, oval-shaped edge 34 which is concentrically-arranged within the outer edge 26 of the impermeable portion 22 and possesses a dimension along each of its major and minor axes which is about one-third the size of the corresponding major or minor axis 36 or 38 of the outer edge 32. Meanwhile, the depth of the concave indentation 34 (as measured from the plane of the surface 56) is about one centimeter, but the indentation 34 can possess an alternative depth.

If desired, the absorbent portion 24 can also be provided with a pull tab 49 disposed adjacent one end thereof for facilitating a removal of the absorbent portion 24 from the impermeable portion 22 following use of the assembly 20.

It is also a feature of the assembly 20 that it includes means, generally indicated 50, for releasably securing the absorbent portion 22 to the concave side face 28 of the impermeable portion 22 so that during use of the assembly 20, the impermeable portion 24 remains securely attached to the side face 28 and so that following the withdrawal of the assembly 20 from a vaginal canal, the absorbent portion 24 can be readily separated from the impermeable portion 22 (by, for example, pulling upon the pull tab 49) so that the absorbent portion 24 can be discarded and the impermeable portion 22, if desired, can be recycled.

Within the depicted assembly 20 and with reference again to FIG. 1, the securing means 50 is in the form of a hook and loop type fastener (such as is available under the trade designation Velcro) including hook-providing portions 52 and loop-providing portions 54, which are attached to the impermeable portion 22 and the absorbent portion 24 for securing the absorbent portion 24 to the impermeable portion 22. More specifically, two hook-providing portions 52 are attached, as with glue, to the side face 28 of the impermeable portion 22, and two loop-providing portions 54 are attached, as with glue, to the underside of the absorbent portion 24 so that upon pressing the absorbent portion 24 against the side face 28, the hook-providing and loop-providing portions 52, 54 cooperate to securely, yet releasably, attach the absorbent portion 24 to the impermeable portion 22.

Figure 2:
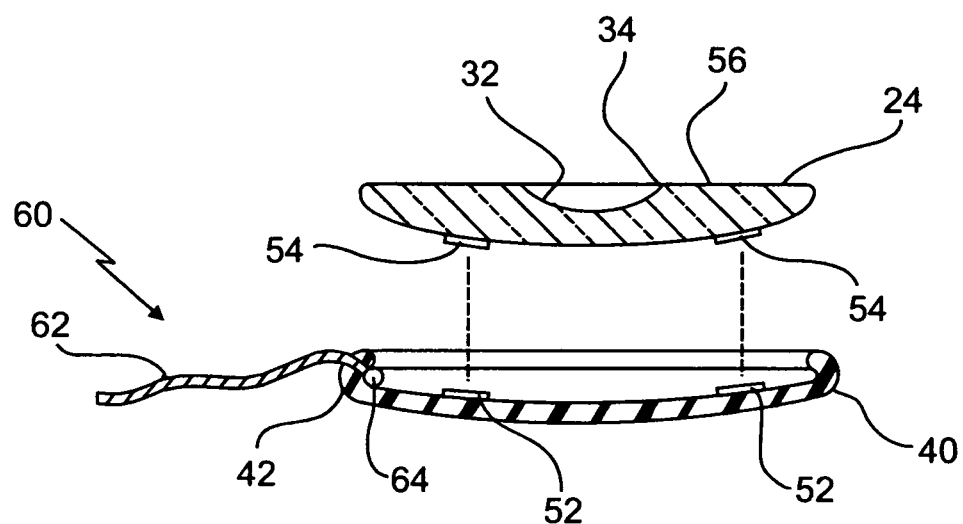
FIG. 2 is a longitudinal cross-sectional view of the FIG. 1 assembly, shown exploded.
Figure 3:
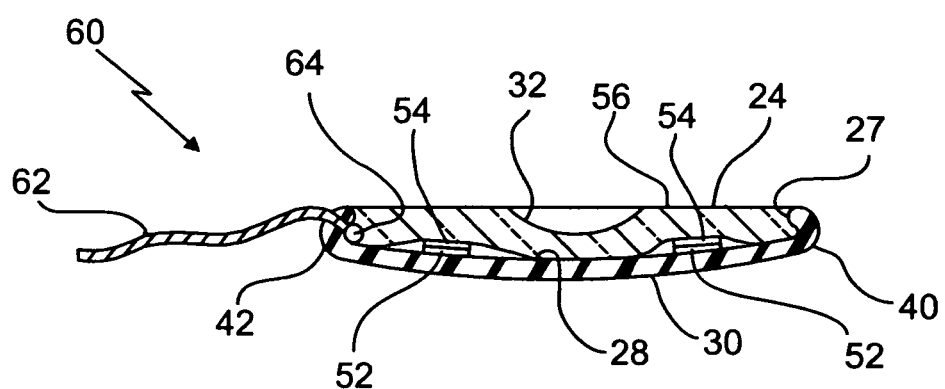
FIG. 3 is a longitudinal cross-sectional view of the FIG. 1 assembly, shown assembled.
Figure 4:
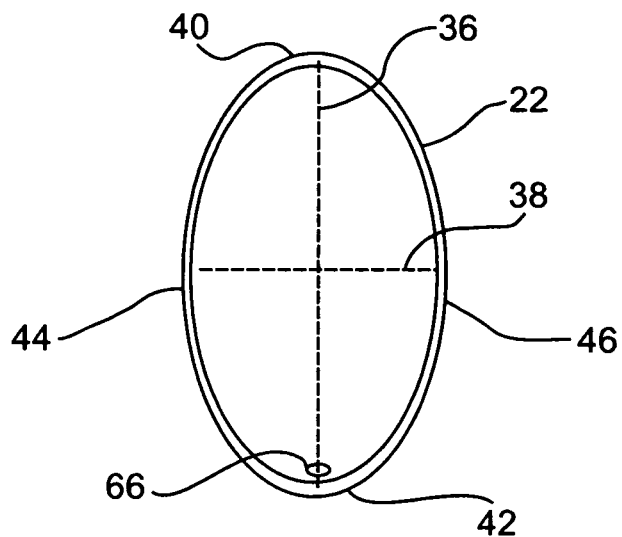
FIG. 4 is a plan view of the impermeable portion of the FIG. 1 assembly as seen generally from above in FIG. 1.

It is an additional feature of the assembly 20 that it also includes means, generally indicated 60 in FIGS. 1 and 2, for facilitating the removal of the assembly 20 from its position of use within the vaginal canal. Within the depicted assembly 20, the facilitating means 60 includes a length of cord or string 62 comprised, for example, of cotton, and which is securely tied or otherwise secured, as with a knot 64 (FIGS. 2 and 3), to the impermeable portion 22 adjacent the trailing end 42 thereof. To facilitate the passing of the string 62 through the impermeable portion 22 for purposes of tying or knotting the string 62, the impermeable portion 22 is provided with a through-opening 66 (FIGS. 1 and 4) adjacent the trailing edge 42 thereof. Because the trailing end 42 of the impermeable portion 22 has been described above as being the end of the impermeable portion 22 which follows the leading end 40 of the impermeable portion 22 into the vaginal canal during installation, the trailing edge 42 is the first end of the impermeable portion 22 which exits the vaginal canal when withdrawn from the user. This being the case, the string 62 provides a visual indication to the user as to which end of the impermeable portion 22 corresponds with the trailing end 24 thereof.

If desired, the entirety of the assembly 20 (i.e. its impermeable portion 22 and absorbent portion 24) can be coated with a thin coating 68 (FIG. 1) of lubricant, such as petroleum jelly, to facilitate the insertion and removal of the assembly 20.

Figure 5:
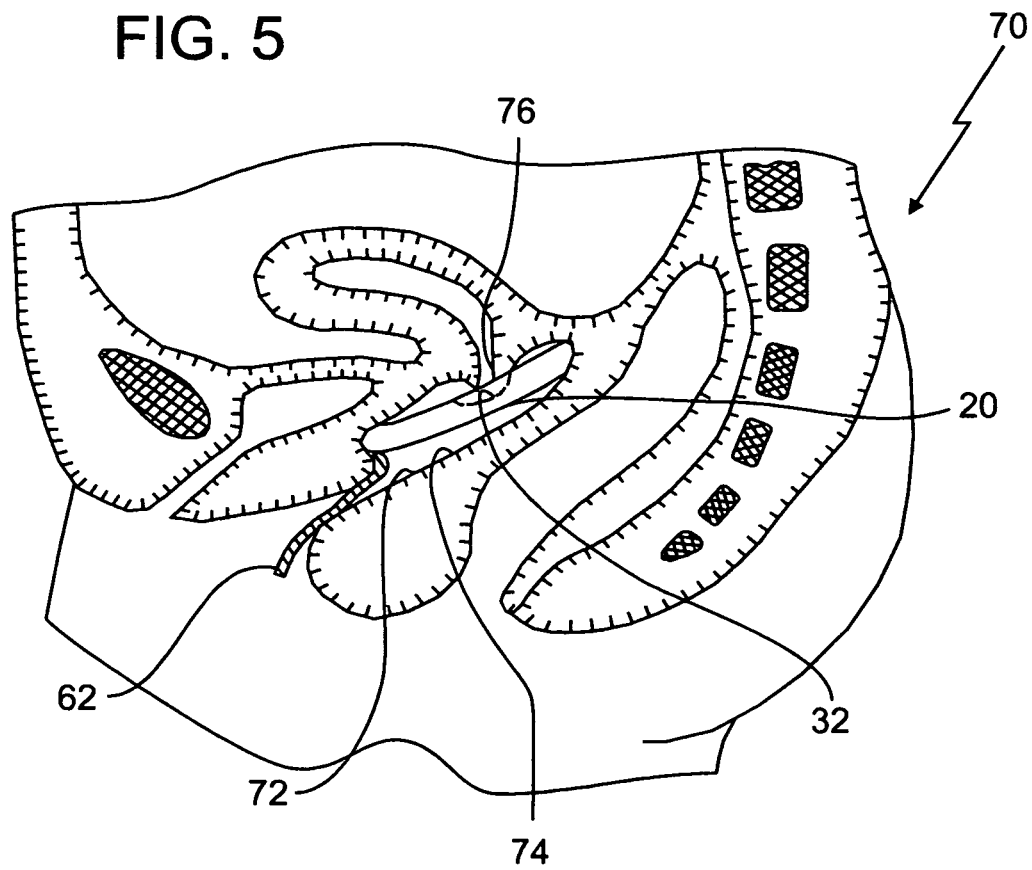
FIG. 5 is a cross-sectional view illustrating schematically the manner in which the FIG. 1 assembly is positioned for use.

With reference to FIG. 5, there is schematically illustrated a cross-sectional portion, indicated 70, of the female anatomy within which the FIG. 1 assembly 20 can be positioned for use. More specifically, the depicted portion 70 includes a vaginal canal 72 having tubular walls 74 and a cervix 76 disposed adjacent the distal, or rearward, end of the vaginal canal 72. When fully positioned within the vaginal canal 72, the outer edge 26 of the impermeable portion 22 bears and rests against the vaginal walls 74 from about the posterior fornix (the vaginal region disposed rearwardly of the cervix 76) to the sub-pubic portion of the upper vaginal wall (i.e. a location disposed immediately behind the pubic bone) and the opening-defining end of the cervix 76 is accepted by the concave indentation 32 of the absorbent portion 24.

With the assembly 20 disposed in the aforedescribed position, the contributions of the oval shape of the outer edge 26 of the impermeable portion 22 and the resilient biasing of the outer edge 26 against the vaginal walls 74 places the outer edge 26 of the impermeable portion 22 in satisfactory sealing relationship with the vaginal walls 74. Furthermore, any discharge from the cervix 76 (whose opening-defining end effectively self-centers itself within the concave indentation 32) is permitted to pool or collect within the indentation 32 for absorption by the material of the absorbent portion 24. Therefore and during use, the absorbent portion 22 is in position to absorb fluid discharged from the cervix 76. Moreover, the assembly 20 is relatively comfortable when used, and if desired, the absorbent portion 24 can be coated with a spermicide and left in place for a prolonged period of time (e.g. up to about six hours) following intercourse for added birth control.

The assembly 20 is readily removed from the vaginal canal 74 in the manner in which a diaphragm is removed, and the removal process is facilitated by the string 62 which can be pulled upon by the user. As mentioned earlier, the absorbent portion 24 can be separated from the impermeable portion 22 by pulling the components 22 and 24 apart (so that the hook-bearing portions 52 and loop-bearing portions 54 are separated from one another) for disposal of the absorbent portion 24 and, if desired, for recycling of the impermeable portion 22.

The tampon assembly 20 can be constructed in any of a number of sizes to accommodate a range of vaginal sizes. For example, the impermeable portion 22 can be sized so that it measures about 65 mm, 75 mm or 85 mm along its major axis 38.

It will be understood that numerous modifications and substitutions can be had to the aforedescribed embodiment 20 without departing from the spirit of the invention. Accordingly, the aforedescribed embodiment 20 is intended for the purpose of illustration and not as limitation.

The invention claimed is:

1. A tampon assembly positionable within the vaginal canal of a user wherein the vaginal canal has a posterior fornix and a sub-pubic portion and walls which extend between the posterior fornix and the sub-pubic portion of the canal, the assembly comprising:

a thin, saucer-shaped impermeable portion having two opposite concave and convex side faces and having an outer edge which is oval in shape so that the oval shape of the impermeable portion has a largest dimension as measured across the center of the impermeable portion and a smallest dimension as measured across the center of the impermeable portion, and the largest dimension is at least about 1.5 times the smallest dimension so as to provide the impermeable portion with a length which corresponds to the largest dimension of the oval shape; and an absorbent portion secured to the concave side face of the impermeable portion so that when the tampon assembly is inserted lengthwise along the vaginal canal so that the largest dimension of the oval shape of the impermeable portion extends along the length of the vaginal canal, the smallest dimension of the oval shape of the impermeable portion facilitates the lengthwise movement of the assembly along the length of the canal, and so that when the tampon assembly is positioned within the vaginal canal for use, the absorbent portion is in position to absorb fluids which exit the cervix without the cervix being encapsulated by the impermeable portion and the outer edge of the impermeable portion is in sealing relationship with the vaginal walls of the user and the largest dimension of the oval shape of the impermeable portion enables the outer edge of the impermeable portion to engage the walls of the vaginal canal from the posterior fornix to the sub-pubic portion thereof; and the absorbent portion is constructed of absorbent material which, when secured to the concave side face of the impermeable portion and the assembly is inserted into place within the vaginal canal, resists deformation of the assembly and thereby renders the assembly capable of strengthening the vaginal walls; and the absorbent portion is sized to substantially fill the concave side face of the impermeable portion and to thereby enhance the fluid-absorbing capacity of the assembly, and means for releasably securing the absorbent portion to the concave side face of the impermeable portion wherein the means for releasably securing includes a hook and loop fastener including a hook-providing portion and a loop-providing portion, and one of the hook-providing portion and the loop-providing portion is attached to the impermeable portion and the other of the hook-providing portion and the loop-providing portion is attached to the absorbent portion.

2. The assembly as defined in claim 1 wherein the largest dimension is about 2.0 times the smallest dimension.

3. The assembly as defined in claim 1 wherein the outer edge of the impermeable portion is elliptical in shape.

4. The assembly as defined in claim 1 wherein the absorbent portion is substantially platen in shape and has an outer edge which is similar in shape to the outer edge of the impermeable portion, and the absorbent portion is positioned against the concave side face of the impermeable portion in a concentric relationship therewith.

5. The assembly as defined in claim 1 further comprising an amount of lubricant which is coated about the impermeable and absorbent portions to facilitate positioning of the assembly within a user and removal of the assembly from a user.

6. The assembly as defined in claim 1 wherein the absorbent portion has a side surface which faces away from the one side of the impermeable portion, and the side surface defines a concave indentation therein which is substantially centrally disposed therein for collecting fluids which exit the cervix.

7. A tampon assembly positionable within a vaginal canal and adjacent the cervix of a user wherein the vaginal canal has a posterior fornix and a sub-pubic portion and walls which extend between the posterior fornix and the sub-pubic portion of the canal, said assembly comprising:
   a flexible and thin, saucer-shaped impermeable portion having two opposite side faces wherein one of the side faces is concave in form and having an outer edge which is oval in shape so that the oval shape of the impermeable portion has a largest dimension as measured across the center of the impermeable portion and a smallest dimension as measured through the center of the impermeable portion, and the largest dimension is at least about 1.5 times the size of the smallest dimension so as to provide the impermeable portion with a length which corresponds to the largest dimension of the oval shape; and
   an absorbent pad portion which is secured to the one concave side face of the impermeable portion so that when the assembly is inserted lengthwise along the vaginal canal so that the largest dimension of the oval shape of the impermeable portion extends along the length of the vaginal canal, the smallest dimension of the oval shape of the impermeable portion facilitates the lengthwise movement of the assembly along the length of the canal, and so that when the assembly is positioned within the vaginal canal for use, the absorbent pad portion is disposed between the cervix and the impermeable portion for absorbing fluids which exit the cervix without the cervix being encapsulated by the impermeable portion, and the outer edge of the impermeable portion sealingly engages the walls of the vaginal canal and the largest dimension of the oval shape of the impermeable portion enables the outer edge of the impermeable portion to engage the walls of the vaginal canal from the posterior fornix to the sub-pubic portion thereof; and
   the absorbent pad portion is constructed of absorbent material which, when secured to the concave side face of the impermeable portion and the assembly is inserted into place within the vaginal canal, resists deformation of the assembly and thereby renders the assembly capable of strengthening the vaginal walls; and
   the absorbent pad portion is sized to substantially fill the concave side face of the impermeable portion and to thereby enhance the fluid-absorbing capacity of the assembly; and
   means for releasably securing the absorbent pad portion to the concave side face of the impermeable portion wherein the means for releasably securing includes a hook and loop fastener including a hook-providing portion and a loop-providing portion, and one of the hook-providing portion and the loop-providing portion is attached to the impermeable portion and the other of the hook-providing portion and the loop-providing portion is attached to the absorbent pad portion.

8. The assembly as defined in claim 7 wherein the largest dimension is about 2.0 times the smallest dimension.

9. The assembly as defined in claim 7 wherein the outer edge of the impermeable portion is elliptical in shape.

10. The assembly as defined in claim 7 wherein the absorbent pad portion is substantially platen in shape and has an outer edge which is similar in shape to the outer edge of the impermeable portion, the absorbent pad portion is positioned against the concave side face of the impermeable portion in a concentric relationship with the outer edge thereof and possesses no part which extends outboard of the outer edge of the impermeable portion.

11. The assembly as defined in claim 10 wherein the impermeable portion includes an inwardly-directed lip which extends along the outer edge, and the absorbent pad portion is captured beneath the inwardly-directed lip when the absorbent pad portion is secured to the one concave side face.

12. The assembly as defined in claim 10 wherein the absorbent pad portion has a side surface which faces away from the one side of the impermeable portion, and the side surface defines a concave indentation therein which is substantially centrally disposed therein for accepting the opening-defining end of the cervix when the assembly is positioned along the vaginal canal.

13. The assembly as defined in claim 7 further comprising an amount of lubricant which is coated about the impermeable and absorbent pad portions to facilitate movement of the assembly along the vaginal canal when the assembly is placed therein or when the assembly is removed therefrom.

14. The assembly as defined in claim 7 wherein the impermeable portion includes a leading end which first enters the vaginal canal when positioned within a user and an opposite trailing end, and the assembly further includes a cord which is securely attached to the impermeable portion adjacent the trailing end thereof for facilitating the removal of the assembly following use.

15. A tampon assembly positionable within a user's vaginal canal having walls and adjacent the cervix for strengthening the walls of the vaginal canal so as to resist deformation of the walls or for collecting cervical cells for laboratory testing purposes wherein the vaginal canal has a posterior fornix and a sub-pubic portion and the walls of the canal extend between the posterior fornix and the sub-pubic portion of the canal, the assembly comprising:
   a flexible and thin, saucer-shaped impermeable portion having two opposite side faces wherein one of the side faces is concave in form and having an outer edge which is oval in shape so that the oval shape of the impermeable portion has a largest dimension as measured across the center of the impermeable portion and a smallest dimension as measured across the center of the impermeable portion, and the largest dimension is at least about 1.5 times the size of the smallest dimension so as to provide the impermeable portion with a length which corresponds to the largest dimension of the oval shape; and
   an absorbent pad portion which is secured to the one concave side face of the impermeable portion so that when the assembly is positioned within a vaginal canal, the absorbent pad portion is disposed between the cervix and the impermeable portion, and the outer edge of the impermeable portion sealingly engages the walls of the vaginal canal;

wherein the absorbent pad portion has a side surface which faces away from the one side of the impermeable portion, and the side surface defines a concave indentation therein which is substantially centrally disposed therein for accepting the opening-defining end of the cervix without the cervix being encapsulated by the impermeable portion when the assembly is positioned along the vaginal canal; and wherein the impermeable portion includes a leading end which first enters the vaginal canal when the assembly is inserted lengthwise into position within the vaginal canal of a user and an opposite trailing end so that when the assembly is inserted lengthwise into the vaginal canal for use, the smallest dimension of the oval shape of the impermeable portion facilitates the lengthwise movement of the assembly along the length of the canal into position therein and so that when the assembly is positioned within the vaginal canal for use, the largest dimension of the oval shape of the impermeable portion enables the outer edge of the impermeable portion to engage the walls of the vaginal canal from the posterior fornix to the sub-pubic portion thereof, and the assembly further includes a cord which is securely attached to the impermeable portion adjacent the trailing end thereof for facilitating the removal of the assembly following use; and the absorbent pad portion is constructed of absorbent material which, when secured to the concave side face of the impermeable portion and the assembly is inserted into place within the vaginal canal, resists deformation of the assembly and thereby renders the assembly capable of strengthening the vaginal walls; and the absorbent pad portion is sized to substantially fill the concave side face of the impermeable portion and to thereby enhance the fluid-absorbing capacity of the assembly; and means for releasably securing the absorbent pad portion to the concave side face of the impermeable portion wherein the means for releasably securing includes a hook and loop fastener including a hook-providing portion and a loop-providing portion, and one of the hook-providing portion and the loop-providing portion is attached to the impermeable portion and the other of the hook-providing portion and the loop-providing portion is attached to the absorbent pad portion.

16. A tampon assembly comprising:

a thin impermeable portion having two opposite side faces and having an outer edge which is oval in shape so that the oval shape of the impermeable portion has a largest dimension as measured across the center of the impermeable portion and a smallest dimension as measured across the center of the impermeable portion, and the largest dimension is at least about 1.5 times the smallest dimension;

an absorbent portion secured to one side face of the impermeable portion so that when the tampon assembly is positioned within a user for use, the absorbent portion is in position to absorb fluids which exit the cervix and the outer edge of the impermeable portion is in sealing relationship with the vaginal walls of the user; and means for releasably securing the absorbent portion to the one side face of the impermeable portion wherein the means for releasably securing includes a hook and loop fastener including a hook-providing portion and a loop-providing portion, and one of the hook-providing portion and the loop-providing portion is attached to the impermeable portion and the other of the hook-providing portion and the loop-providing portion is attached to the absorbent portion.

* * * * *